US00PP20944P2

(12) United States Plant Patent
Leinert

(10) Patent No.: US PP20,944 P2
(45) Date of Patent: Apr. 27, 2010

(54) *EUPHORBIA* PLANT NAMED 'SILVERSHADOW'

(50) Latin Name: *Chamaesyce hypericifolia*
Varietal Denomination: Silvershadow

(76) Inventor: Uwe Leinert, Rosenweg 2, D-74918 Angelbachtal (DE)

( * ) Notice: Subject to any disclaimer, the term of this patent is extended or adjusted under 35 U.S.C. 154(b) by 0 days.

(21) Appl. No.: 12/313,682

(22) Filed: Nov. 21, 2008

(51) Int. Cl.
*A01H 5/00* (2006.01)

(52) U.S. Cl. ..... Plt./263.1

(58) Field of Classification Search ..... Plt./263.1, Plt./302
See application file for complete search history.

(56) References Cited

OTHER PUBLICATIONS

Upov-rom Plant Variety Database 2009/03. GTI Jouve Retrival Software, Citation for *Chamaesyce* 'Silvershadow' one page.*

* cited by examiner

*Primary Examiner*—June Hwu
(74) *Attorney, Agent, or Firm*—C. A. Whealy

(57) ABSTRACT

A new and distinct cultivar of *Euphorbia* plant named 'Silvershadow', characterized by its upright, outwardly spreading and mounding plant habit; vigorous growth habit; freely branching habit; and numerous white-colored flowers.

1 Drawing Sheet

Botanical designation: *Chamaesyce hypericifolia.*
Cultivar denomination: 'Silvershadow'.

CROSS-REFERENCED TO RELATED APPLICATIONS:

Title: *Euphorbia* Plant Named 'Silverfog'
Applicant: Uwe Leinert
Filed: Concurrently with this application (U.S. Plant patent application Ser. No. 12/313,684)

BACKGROUND OF THE INVENTION

The present invention relates to a new and distinct cultivar of *Euphorbia* plant, botanically known as *Chamaesyce hypericifolia* and hereinafter referred to by the name 'Silvershadow'.

The new *Euphorbia* plant is a product of a planned breeding program conducted by the Inventor in Angelbachtal, Germany. The objective of the breeding program is to create new compact *Euphorbia* cultivars with freely branching habit and numerous flowers.

The new *Euphorbia* plant originated from an open-pollination made in June, 2006 in Angelbachtal, Germany of a proprietary selection of *Chamaesyce hypericifolia* identified as code number F-04-06, not patented, as the female, or seed, parent with an unknown selection of *Chamaesyce hypericifolia* as the male, or pollen, parent. The new *Euphorbia* was discovered and selected by the Inventor as a single flowering plant from within the progeny of the stated open-pollination in a controlled greenhouse environment in Angelbachtal, Germany in October, 2006.

Asexual reproduction of the new *Euphorbia* plant by vegetative cuttings in a controlled greenhouse environment in Rheinberg, Germany since August, 2007, has shown that the unique features of this new *Euphorbia* plant are stable and reproduced true to type in successive generations.

SUMMARY OF THE INVENTION

Plants of the new *Euphorbia* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Silvershadow'. These characteristics in combination distinguish 'Silvershadow' as a new and distinct cultivar of *Euphorbia:*

1. Upright, outwardly spreading and mounding plant habit.
2. Vigorous growth habit.
3. Freely branching habit.
4. Numerous white-colored flowers.

The new *Euphorbia* can be compared to plants of the female parent selection. Plants of the new *Euphorbia* differ primarily from plants of the female parent selection in the following characteristics:

1. Plants of the new *Euphorbia* are more compact than plants of the female parent selection.
2. Plants of the new *Euphorbia* have smaller leaves than plants of the female parent selection.

Plants of the new *Euphorbia* can be compared to plants of *Chamaesyce hypericifolia* 'Silverfog', disclosed in a U.S. Plant patent application filed concurrently. Plants of the new *Euphorbia* differ from plants of 'Silverfog' in the following characteristics:

1. Plants of the new *Euphorbia* are more vigorous than plants of 'Silverfog'.
2. Plants of the new *Euphorbia* have larger leaves than plants of 'Silverfog'.
3. Plants of the new *Euphorbia* have shorter flower bracts than plants of 'Silverfog'.

Plants of the new *Euphorbia* can also be compared to plants of the *Euphorbia* 'Inneuphdia', disclosed in U.S. Plant Pat. No. 17,567. Plants of the new *Euphorbia* differ from plants of 'Inneuphdia' in the following characteristics:

1. Plants of the new *Euphorbia* are more vigorous than plants of 'Inneuphdia'.
2. Plants of the new *Euphorbia* have smaller and narrower leaves with shorter petioles than plants of 'Inneuphdia'.

3. Plants of the new *Euphorbia* have shorter flower bracts than plants of 'Inneuphdia'.

BRIEF DESCRIPTION OF THE PHOTOGRAPH

The accompanying colored photograph illustrates the overall appearance of the new *Euphorbia,* showing the colors as true as it is reasonably possible to obtain in colored reproductions of this type. Colors in the photograph may differ slightly from the color values cited in the detailed botanical description which accurately describe the colors of the new *Euphorbia*

The photograph is a side perspective view of a typical flowering lateral plant of 'Silvershadow' grown in a container.

DETAILED BOTANICAL DESCRIPTION

The aforementioned photograph and following observations, measurements and values describe plants grown in Rheinberg, Germany, under commercial practice during the winter in a glass-covered greenhouse with day and night temperatures averaging 22° C. and light levels averaging 4,500 lux. Rooted young plants were pinched one time about five weeks after planting and plants had been growing for 16 weeks when the photograph and description were taken. In the following description, color references are made to The Royal Horticultural Society Colour Chart, 1995 Edition, except where general terms of ordinary dictionary significance are used.

Botanical classification: *Chamaesyce hypericifolia* 'Silvershadow'.

Parentage:

*Female, or seed, parent.*—Proprietary selection of *Chamaesyce hypericifolia* identified as code number F-04-06, not patented.

*Male, or pollen, parent.*—Unknown selection of *Chamaesyce hypericifolia*, not patented.

Propagation:

*Type.*—By vegetative cuttings.

*Time to initiate roots, summer.*—About nine days at 22° C.

*Time to initiate roots, winter.*—About 13 days at 22° C.

*Time to produce a rooted young plant, summer.*—About three weeks at temperatures of 22° C.

*Time to produce a rooted young plant, winter.*—About four weeks at temperatures of 22° C.

*Root description.*—Medium in thickness, fleshy, fibrous; white in color.

*Rooting habit.*—Freely branching; dense.

Plant description:

*Plant form and growth habit.*—Mounding plant habit; plants upright to outwardly spreading; broad inverted triangle; vigorous growth habit.

*Branching habit.*—Freely branching, usually about three to five primary branches each with numerous secondary and tertiary lateral branches developing per plant.

*Plant height.*—About 18 cm.

*Plant diameter.*—About 35 cm.

*Lateral branch description.*—Length: About 15 cm. Diameter: About 3 mm. Internode length: About 2.8 cm. Strength: Strong. Texture: Smooth, glabrous. Color: Close to 146A.

Foliage description:

*Arrangement.*—Opposite; simple.

*Length.*—About 2.6 cm.

*Width.*—About 1.4 cm.

*Shape.*—Elliptical.

*Apex.*—Acute.

*Base.*—Attenuate to acute.

*Margin.*—Entire.

*Texture, upper and lower surfaces.*—Pubescent.

*Venation.*—Pinnate, arcuate.

*Color.*—Developing leaves, upper surface: Close to 146A. Developing leaves, lower surface: Close to 146B. Fully developed leaves, upper surface: Close to 147A; venation, close to 147A. Fully developed leaves, lower surface: Close to 147B; venation, close to 147C.

*Petioles.*—Length: About 1.5 cm. Diameter: About 1 mm. Texture, upper and lower surfaces: Pubescent. Color, upper and lower surfaces: Close to 146A.

Inflorescence description:

*Flower arrangement/habit.*—Single rotate flowers arranged in umbel-like compound terminal cymes. Very freely flowering with numerous flower buds and flowers per plant. Flowers face upright and outwardly.

*Fragrance.*—Not detected.

*Natural flowering season.*—Spring and summer in Germany; flowering continuous during this period.

*Flower longevity on the plant.*—About ten days; flowers persistent.

*Flower diameter.*—About 1.9 cm.

*Flower depth* (*height*).—About 1 cm.

*Floral bracts.*—Quantity/arrangement: Two; opposite. Length: About 7.25 mm. Width: About 2 mm. Shape: Elliptical to lanceolate. Apex: Rounded to acute. Base: Fused. Margin: Entire. Texture, upper and lower surfaces: Glabrous; smooth. Color: When opening and fully expanded, upper surface: Close to 155D. When opening and fully opened, lower surface: Close to 155D. Floral bract petioles: Length: About 2 mm. Diameter: About 1 mm. Color: Close to 146B to 146C.

*Peduncles.*—Length: About 2.5 cm. Diameter: About 1 mm. Strength: Strong. Angle: About 60° to 90° from vertical. Texture: Smooth, glabrous. Color: Close to 146A.

*Cyathia.*—Length: About 4 mm. Diameter: About 3 mm. Shape: Oval. Aspect: Upright. Color, immature and mature: Close to 144A.

*Nectaries.*—Quantity per flower: About four. Shape: Lunate. Length: About 1 mm. Width: About 2 mm. Color: Close to 146A; towards the apices, close to 155D.

*Reproductive organs.*—Androecium: Quantity: About four stamens per cyathia. Shape: Oval, bi-lobed. Length: Less than 1 mm. Color: Close to 158C. Pollen: Scarce. Pollen color: Close to 158D. Gynoecium: Quantity: One per cyathia. Pistil length: About 3 mm. Style length: Less than 1 mm. Style color: Close to 155D. Stigma shape: Crested. Stigma color: Close to 155D. Ovary color: Close to 144A. Seed/fruit: Seed and fruit development have not been observed on plants of the new *Euphorbia*

Temperature tolerance: Plants of the new *Euphorbia* have been observed to have tolerate temperatures ranging from about 12° C. to about 40° C.

Pathogen/pest resistance: Plants of the new *Euphorbia* have not been observed to be resistant to pathogens and pests common to *Euphorbia.*

It is claimed:

1. A new and distinct *Euphorbia* plant named 'Silvershadow' as illustrated and described.

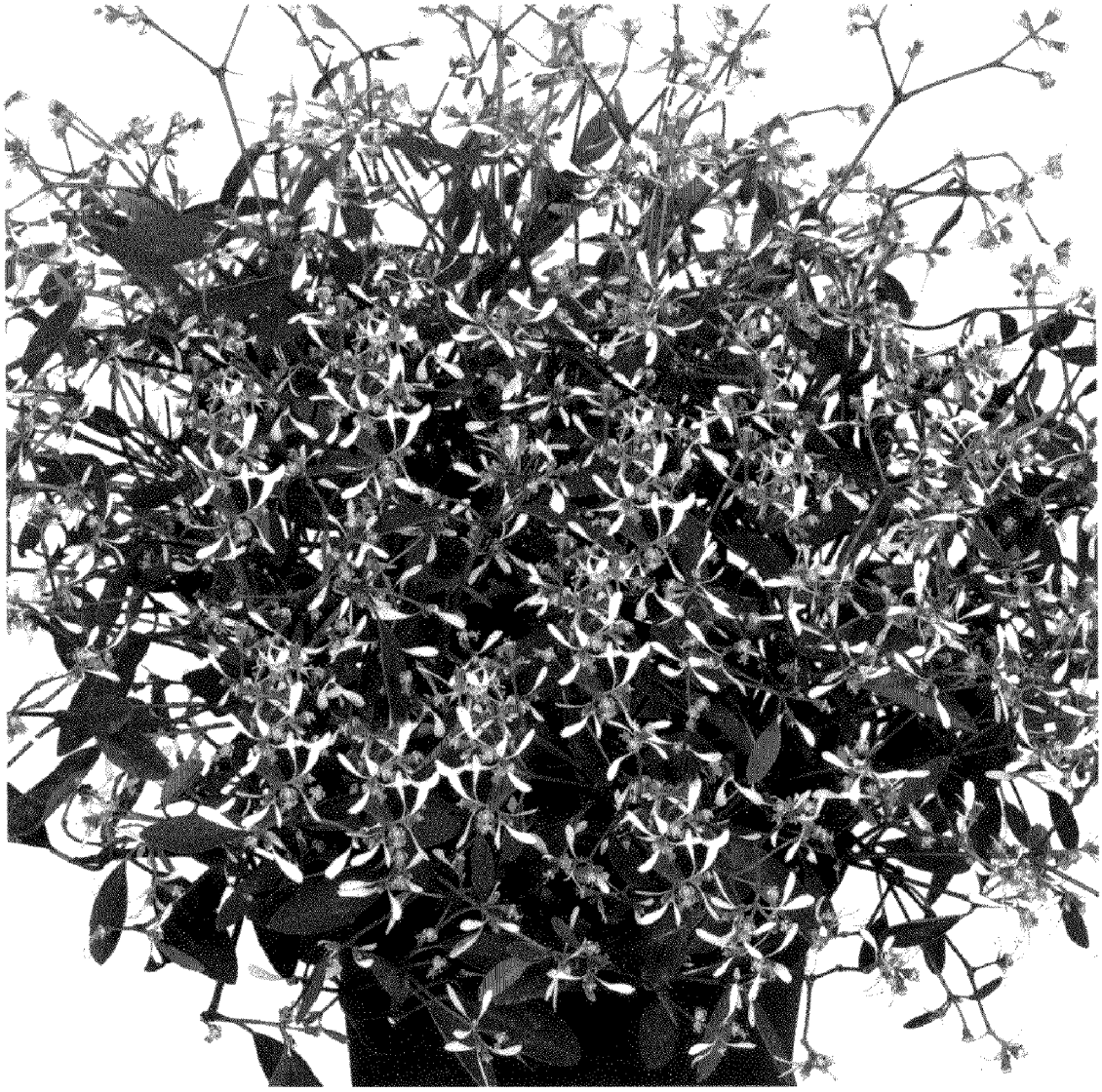

* * * * *